United States Patent [19]

Schmidt et al.

[11] 4,183,431
[45] Jan. 15, 1980

[54] ACCESS SUTURE PACKAGE

[75] Inventors: Rolf D. Schmidt, Mohnton; Earl M. Theodore, Reading, both of Pa.

[73] Assignee: Sharpoint, Inc., Mohnton, Pa.

[21] Appl. No.: 914,276

[22] Filed: Jun. 9, 1978

[51] Int. Cl.² .............................................. A61L 17/02
[52] U.S. Cl. .................................. 206/63.3; 206/227; 206/382; 43/57.5 R
[58] Field of Search ...................... 206/63.3, 227, 380, 206/382, 383; 43/57.5 R

[56] References Cited

U.S. PATENT DOCUMENTS

| | | | |
|---|---|---|---|
| 3,180,487 | 4/1965 | Uddenborg | 206/227 |
| 3,819,039 | 6/1974 | Erickson | 206/438 |
| 3,951,261 | 4/1976 | Mandel et al. | 206/370 |
| 3,985,227 | 10/1976 | Thyen et al. | 206/227 |

*Primary Examiner*—William T. Dixson, Jr.

*Attorney, Agent, or Firm*—M. Richard Page

[57] ABSTRACT

Surgical sutures are protected from damage in shipment and handling by providing holders having foamed plastic shapes that are adapted to receive the point and cutting surfaces of a needle in an edge portion of the foamed plastic shape and retain the suture in a manner so that the suture can be easily removed from the holder without the need for undue manipulation of the holder. The holders may also serve as a support to facilitate the manipulation of the needle or suture by operating room personnel, to organize and provide access to selected lengths of surgical thread, and to provide an identifiable repository for used needles. The foamed plastic protective handling devices of this invention are particularly suitable for use in cooperative relationship with selected packaging materials to permit the storage of needles and sutures under sterile conditions.

9 Claims, 5 Drawing Figures

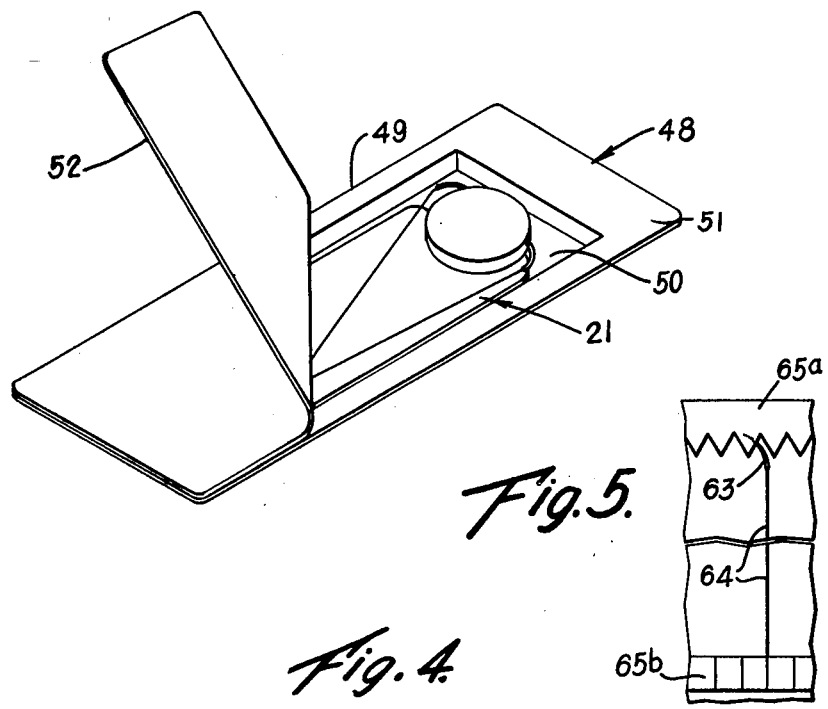
Fig. 3.
Fig. 5.
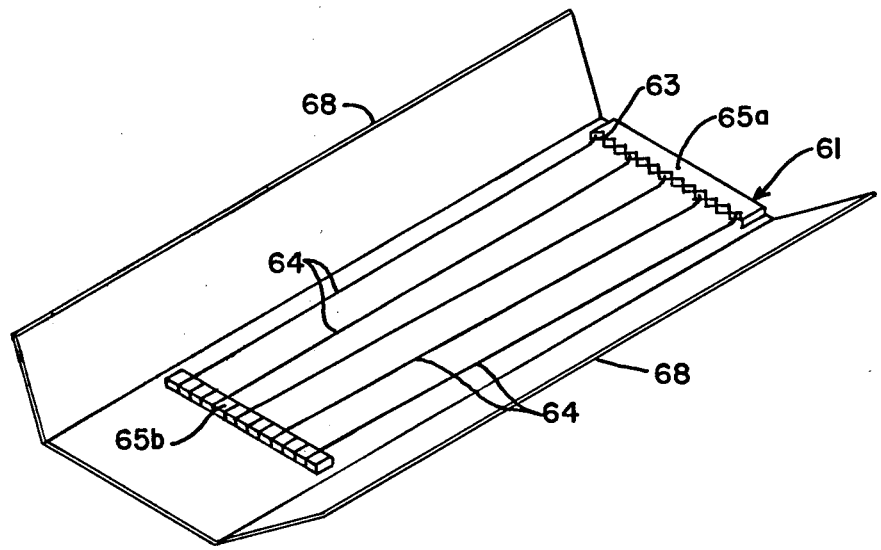
Fig. 4.

ACCESS SUTURE PACKAGE

DEFINITIONS

For purposes of this specification and the appended claims, the following terms are defined as follows:

"Needle" is used to mean a surgical needle only.

"Surgical thread" is used to mean a ligature, thread or monofilament suitable for sewing the lips of a wound together. It may be either absorbable or nonabsorbable.

"Suture" is used to mean the assembly of a needle and a surgical thread.

"Double-armed suture" is used to mean a suture that has a needle mounted at each end of the surgical thread.

BACKGROUND OF THE INVENTION

1. Field of the Invention

This invention relates to methods and means for packaging surgical needles and sutures, and, more particularly, to protective packaging devices that may serve to facilitate manipulation and removal and to account for and dispose of surgical needles and sutures.

2. Description of the Prior Art

To reduce the time of operative procedures and to permit surgeons to utilize their skills more effectively, it has become increasingly common practice to package surgical tools and appliances in a manner in which they are most readily accessible to operating room personnel. In addition to using packaging techniques that permit the operating room nurse and the surgeon to manipulate the various surgical devices, the devices are packaged in a sterile environment so that the devices are immediately available for use as may be required. This simplifies older techniques in which the requirements of a given operative procedure have to be anticipated and the various tools and appliances that will be used are sterilized and made ready for use prior to the operation.

The packaging trend has advanced to the extent that entire kits are assembled containing all appliances and tools that will be needed for a given operative process. In many cases, it is more efficient and less expensive to include sterile disposable items in kit form than it is to clean and sterilize individual surgical devices for reuse. A primary advantage that is gained is that a surgeon is assured that all of his requirements for special tools and appliances will be readily available to him during an operation without advance preparation or running down a check list. A secondary advantage is that, since the contents of a kit are all readily identifiable, it is comparatively simple to account for all of the tools and appliances that have been used during an operation and reduce the possibility of leaving a device within the patient.

In keeping with the above thinking, it has become rather common practice to package and store surgical needles and sutures in sterile packages. These packages are designed to permit sterilizing the contents and maintaining the contents in a sterile condition until they are removed for use. In one well-recognized method for the sterile packaging of needles and sutures, the needle or suture is sealed within a protective envelope having at least one portion which is pervious to sterilizing gas, such as ethylene oxide, but which is impervious to the passage of bacteria. An example of these gas-pervious, bacteria-impervious materials is a spun bonded polyolefin material sold by DuPont under its trademark "Tyvek". To utilize this type of material, a surgical device, such as a needle or suture, is placed in an impervious tray or tub and a film of the gas-pervious, bacteria-impervious paper or plastic is sealed to flanged edges of the tray. The sealed package is then exposed to ethylene oxide which permeates the paper or plastic and sterilizes the contents of the package. Since the paper or plastic is designed to prevent the passage of bacteria, the contents of the package will remain sterile until the seal is broken.

Depending upon the preference of the surgeon and the type of wound to be closed, the needle may contain an eye for threading a surgical thread through the needle or, particularly in more delicate operations, the needle may be packaged as a suture with the surgical thread attached to the needle.

Sometimes a needle is affixed at each end of the surgical thread to provide a double-armed suture which allows a wound to be closed by using both ends of the surgical thread. These double-armed sutures are also convenient since they make two sutures readily available when the surgical thread is cut at any selected point between the two needles.

The techniques of enclosing and storing a needle or suture within a package that may be sterilized are well developed in the prior art and do not, in themselves, form a part of this invention. Rather, this invention is concerned with methods for mounting a suture on a holding device that, in addition to further advantages discussed below, will protect the point of the needle, will act as a holding device to permit manipulation of the suture, and will form a support on which the surgical thread is organized to avoid tangles, snags or permanent deformation, yet allow rapid removal of the suture without the need for manipulating the holder.

Numerous patents may be found in the prior art that adequately perform certain of these functions to varying degrees, but none of them do all of them well. Also, needle and suture packages employing sterile, non-sloughing foam materials as a holder are found in the prior art. In one such package, two eyed needles were carried on opposed side edges of a planar sheet of such foam material. The foam sheet was used to retain and protect the points and eyes of the needles during shipment and to hold the needles for threading by the surgeon. Also, strips of such materials have been used for packaging sutures, and particularly double-armed sutures. One such design comprises a sheet of foamed material having recessed portions on opposed edges adjacent one end of the sheet. Three retaining slits for retaining the surgical thread are located in the ends of the strip of foam. This design has the disadvantage that it requires undue manipulation of the package in order to remove a suture; the needle is grasped by the surgeon and the thread must then be unwound from the foam strip. The suture of usage length cannot readily be removed from the package by merely exerting an axial pull on the suture.

OBJECTS OF THE INVENTION

It is an object of this invention to provide a suture package which will protect the suture from damage yet allow rapid removal of the suture by the surgeon without manipulation of the package.

Another object of this invention is to provide a suture holder that may be used as a support to facilitate obtaining a purchase on the needle or for reinserting the needle to gain a new purchase of different attitude.

Another object of this invention is to provide a holding device that will retain a suture in a secure position (i.e., prevent the contents from tumbling out of the package) when the package is opened.

Another object of this invention is to provide a holding device for a suture that will releasably secure a surgical thread in an organized manner for convenient removal without kinking or permanently deforming the surgical thread.

Another object of this invention is to provide a needle or suture holder that carries visual identification, as by printing or color coding, of the type and size of the needle or surgical thread.

Another object of this invention is to provide a needle or suture holder which has a portion that is opaque to X-rays and may be readily located if accidentally closed within a wound.

Another object of this invention is to provide a repository for used needles or sutures which will provide identification and accountability of the needles or sutures used during surgery.

Another object of this invention is to provide a holder for the needle of a suture that may be used to hold the needle between passes of the suture if the attitude of the needle need be adjusted or reversed.

Another object of this invention is to produce holders having the foregoing characteristics at low cost.

SUMMARY OF THE INVENTION

Briefly, these and other objects of this invention are achieved by providing a shaped piece of low-density foamed plastic material into which a needle is inserted and protectively held without damaging the point or cutting edges of the needle. The foamed plastic is selected so that no debris will slough off and contaminate the operational environment with foreign matter when the needle is inserted, removed or reinserted.

The foam, because of its low density, will accept the point of a needle without damage or loss of sharpness to the point and cutting surfaces, but will, at the same time, absorb impact forces and protect the needle from damage. Also, due to the low density of the foam, the holder will float on a liquid to facilitate dyeing the surgical thread.

In one embodiment of this invention, the piece of foamed plastic may be rather small compared with the needle and the piece of foamed plastic mounted on a sheet of larger material. This larger sheet may optionally include another piece of foamed plastic located remotely from the needle holder which is suitable for receiving and holding the end or turns of surgical thread. If the sheet is made sufficiently wide, it may be folded over the needle or sutures to provide additional protection.

Needles and suture holders of this type may be identified as to their type and size by color coding or printing on the holder or by printing on a sheet or film which is adhered to a back portion of the holder. In this latter instance, the sheet can be wrapped around the needle or suture to give further protection against damage Additional identification, such as a metallized film of plastic, may be attached to the holder or the sheet surrounding it so that the holder may be located by X-ray should it inadvertently be enclosed within a wound during surgery.

The foamed plastic is adapted to receive the needle in a portion of its edge and the thickness of the piece of foamed plastic should be at least as great, and preferably greater, than the largest diameter of the needle so that when a needle or suture is stored within the package, not only the point, but also the shank of the needle is protected from damage as by bending or twisting forces.

Since the needle or suture may readily be reinserted into the foamed plastic of the holder, the holder may be used to reinsert a needle when the surgeon desires to adjust the attitude of the needle between successive stitches. Conveniently, the holder may be anchored to a surface, or, for that matter, taped to the patient at a location convenient to the incision or wound being closed.

The holder is designed so that the suture is protected against contact with other portions of the sterile packaging. This substantially eliminates abrasion of the suture and dislodgement from the holder.

The holder may also be used as a receptacle for used needles and sutures. This can be of great help in accounting for all of the needles and sutures that were used during an operation, particularly if the holder bears permanent indicia identifying the kind of needle or suture. The sutures are arranged on the holder so that the indicia is not obscured by the sutures.

There is no criticality as to the type of plastic foam which can be used in making the needle holder, provided that it is or can be sterilized, that it is soft enough to receive and hold a needle without damage to the cutting edges of the needle, and that it is of sufficient cohesive strength to hold together and not crumble or release debris when a needle is inserted or removed. One particularly suitable foam for use in this invention is a closed-cell foam sold under the trademark "Volara" by Voltek. This foam is especially preferred since the plastic is foamed by irradiation and the interior portion of the foam is sterilized during manufacture.

DESCRIPTION OF THE DRAWINGS

The above-mentioned objects and other objects of this invention can more readily be understood from the following description of the drawings, in which:

FIG. 3 is a perspective view of a completed package, partially opened, containing a needle holder made in accordance with this invention;

FIG. 4 is a perspective view of a needle holder with a protective wrap-around sheet adapted to contain and organize a plurality of sutures; and FIG. 5 is a fragmentary view of the suture package of FIG. 4 showing the mounting of a single suture.

Figure 1:
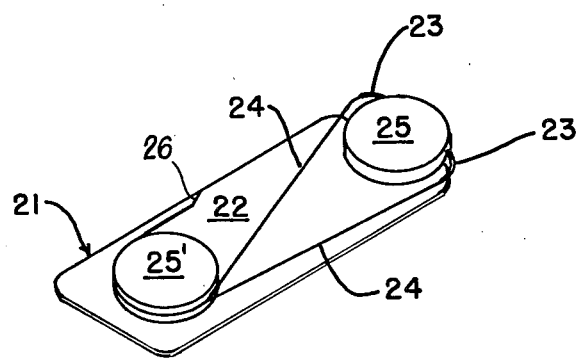
FIG. 1 is a perspective view of one embodiment of the invention in which a double-armed suture is secured by a holder in accordance with this invention.

One embodiment of a holding device made in accordance with this invention is illustrated in FIG. 1 in which two round discs 25, 25' are cut from a sheet of plastic and mounted on a thin, relatively stiff support 22. The needles 23 of the suture are inserted into the sides of one of the discs 25. The other disc then serves as a wrapping means and the surgical thread is wound preferably about a portion of the peripheral edge of disc 25'. The thread extends from disc 25' and is lightly frictionally retained in a single retaining means, such as slit 26 in the support 22.

The suture may either be single- or double-armed. In either case, the end of the surgical thread extends somewhat beyond the slit 26, but is free of further attachment to the package. It should be noted that in this design, to remove the suture, the surgeon merely obtains a purchase on one of the needles and pulls it and the accompanying surgical thread in straight line fashion away from the discs 25, 25'. There is no need to manipulate the package to unwind the suture. Of course, if the suture is double-armed, the surgical thread may be cut prior to removal at the desired point—for example, at the loop of thread that extends beyond the retaining slit 26. The retaining slit lightly frictionally engages the thread and the thread can readily be withdrawn.

While substantially any appropriate means can be utilized to secure the discs 25, 25' to the support 22, it has been found advantageous to employ material to form the support 22 that has a layer of thermoplastic material on the upper surface so that the discs can be heat sealed directly onto the sheet 22. Preferably, the disc 25 is wholly or partly, and the disc 25' is wholly, mounted inboard of the edges of support 22. This yields the advantage that the needles and a substantial length of the surgical thread are protected against contact with other parts of the sterile packaging—for example, the plastic tub 49 and cover sheet 52 shown in FIG. 3. This lessens the likelihood that the surgical thread will become abraded or the sutures dislodged during shipment. Further, needles are visible from both sides of sheet 22 when disc 25 is mounted partly aboard of sheet 22.

In addition, this package design is adaptable for use with more than two sutures. A plurality of needles can be placed in the disc 25 and the attached sutures extend, preferably all in the same direction, around a portion of the wrapping disc 25'. Such a mounting lessens the likelihood of tangling, kinking or deforming of the surgical thread as the suture is removed from the package.

It should also be realized that this design facilitates labeling of the package, as there is sufficient space between the discs 25, 25' for applying a suitable label. It is important to retain such a label with the needle holder because the labels commonly give the type and quantity of needles in the original package, thereby facilitating recovery and accountability after the surgical procedure is terminated.

Also, because the edge portions of the discs 25, 25' are within the peripheral edges of the support 22, safety of disposal of used needles is enhanced because there is less likelihood of a needle's being presented in a position to puncture the skin of the disposing party.

Another advantage of this design is that it minimizes the amount of foam material necessary to retain the sutures. As the foam material is one of the higher cost elements of the packaging, this reduces packaging costs.

Figure 2:
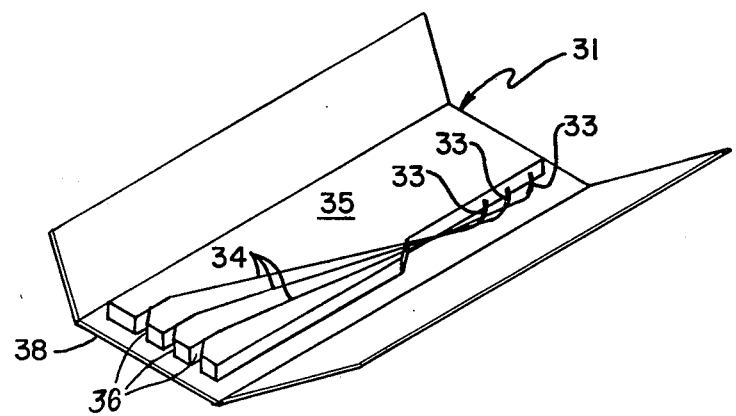
FIG. 2 is a perspective view of another embodiment of this invention in which the needle holder is made from a strip of plastic foam mounted on a larger sheet of material adapted to wrap around and protect the suture.

Another form of this invention is illustrated in FIG. 2 in which the holder 31 includes a foamed sheet 35 mounted upon a foldable sheet of foil 38. Needles 33 are inserted into an edge portion, partially cut away to protect the needle 33, and the surgical thread 34 is would around a side portion of the foamed sheet 35. The paper or foil 38 is partially adhered to the back side of the plastic sheet 35 adjacent the edge opposite the one that serves to hold the surgical thread 34 so that the thread is not adhered to the package.

The film or foil 38 preferably is made to be folded over the assembled sutures for added protection and also to enable the holding device to be manipulated without touching the sterilized sutures. This will permit a nurse to handle the exterior of a package, remove the composite device 31 and grasp it by the side edges of the film sheet or foil 38 to expose the contents for removal by the sterile nurse or the surgeon.

As illustrated in FIG. 2, the foil has a first portion in which the foamed sheet 35 is secured. If the foil has a layer of a thermoplastic material on one surface, the sheet 35 can be heat-sealed directly to the foil. A second portion of the foil is then folded over the sheet 35. It is especially advantageous to mount the foamed sheet 35 so that the cut-away portion that receives the needles is disposed adjacent the fold line between the two portions of foil. In this manner, the fold protects the needles and sutures against abrasion and dislodgements.

In this form of package, the surgical thread extends from the needles 33 to the retaining slits 36 formed in the foam material 35, which slits lightly frictionally retain the surgical thread. Alternatively, a single slit for holding a plurality of threads can be utilized. It should be noted that in removing a suture from this package, one merely unfolds the foil wrapping, obtains a purchase on one of the needles, and then pulls the suture directly, with a straight line motion, extending in the direction from the cut-away portion to the edge of the foam material carrying the slits 36. There is no need to manipulate the package to unwind the suture.

It should also be realized that this form of packaging simplifies the application of identifying labels to the package. This is so because there is a relatively large, clear area of the foam material adjacent the cut-away portion that is adapted for receiving suitable labels.

It should also be noted that this package design reduces the likelihood of the suture becoming kinked. Also, in this design, the suture is carried entirely within the peripheral edges of the package and thus does not come into contact with other sterile portions of the packaging.

FIG. 3 illustrates a device 48 for packaging the holding devices of this invention. The packaging device 48 is comprised of an impervious tub 49 having a recessed portion 50 and flanges 51. The tub 49 may be made, for example, from plastic film or thin sheet as may be shaped by vacuum forming. The tube is suitably dimensioned to receive a holding device of this invention, here shown as device 11, as more fully discussed with respect to FIG. 2 above. A sheet of gas-pervious and bacteria-impervious material 52 covers the opening of the tub 49 and is heat-sealed to the flanges 51. After the suture-holding device 21 is inserted in the tub and the paper sealed over it, the sealed package may be placed in an atmosphere of ethylene oxide which will permeate the paper 52 and sterilize the contents of the container. The contents will remain sterilized until the plastic paper material 52 is peeled away from the tub 49.

Still another variation of the suture holder of this invention is illustrated in FIG. 4 where the suture holder 61 is comprised of a sheet of material 68 that serves as a support for a pair of plastic foamed suture holders 65a and 65b. As illustrated in the drawing, the suture holding element 65a has a scalloped or serrated edge, but can be of other configurations to enable the needles 63 of the suture to be inserted into the side of the needle holder 65a. The foamed plastic strip 65b mounted at the other end of the film 68 serves to secure the free end of the surgical thread 64 of the suture. As discussed in connection with FIG. 4, the film 68 is adapted to be folded in protective relationship over the suture to permit handling without touching the sterilized contents of the holding device 61. An advantage of the scalloped or serrated edge is that quite a number of sutures can be packaged in side-by-side relationship. Also, as shown in FIG. 5, the surgical thread 64 extends from the needle 63 to the retaining means 65b in a manner so that the thread is substantially aligned with respect to the axis of the needle at the point of attachment of the thread to the needle. This lessens the likelihood that the thread will be abraded by the end of the needle and break away from the needle as the suture is quickly withdrawn from the package.

As in previous examples, preferably the foil material 68 carries a layer of thermoplastic material to which the foam strips 65a and 65b are heat-sealed. Also, depending upon the length of the suture, it has been found desirable to incorporate an intermediate retaining strip, similar to strip 65b, intermediate strips 65a and 65b.

This form of packaging has substantial benefits in terms of presenting a relatively large number of sutures in a manner providing for optimum presentation of the suture and rapid, straight-line withdrawal of the suture from the package, without tangling.

From the foregoing description of the drawings, it can be understood how the objects of this invention are achieved utilizing foamed sheet materials of various configurations mounted upon a protective sheet. In all cases, a free edge of the foam is exposed to receive and protect the pointed end of a needle and its cutting surfaces. When a suture is mounted on the holding device, the holding device also serves to organize the surgical thread of the suture and permit its ready withdrawal for use by a simple straight line motion. The foamed suture holder may also serve to facilitate maneuvering the needle or suture or to reinsert the needle after initial removal for any manipulative purpose. The sutures are protected against abrasion with parts of the sterile packaging. The packages also present clear surfaces for readily receiving suitable labeling. At the end of the surgical procedure, the used needles or sutures may be inserted into the holding device for ready accountability of the needles or sutures that have been used during the operation. Packages having these advantages are produced at relatively lower cost.

We claim:

1. A suture package comprising:
   a support element;
   a needle-receiving member mounted on the support element, the needle-receiving member comprising a body of pierceable, nonsloughing material;
   a needle, a portion of which is inserted into a side surface of the needle-receiving member, the thickness dimension of the needle-receiving member being greater than the diameter of the needle;
   a length of surgical thread attached to the needle;
   a wrapping means mounted on the support member, the wrapping means comprising a body having a peripheral wrapping surface; and
   thread-retaining means on the support element for lightly frictionally retaining a portion of the thread, the thread extending from the needle and passing about at least a portion of the peripheral surface of the wrapping member and thence to the thread-retaining means.

2. A suture package as in claim 1 wherein the portion of the peripheral surface that receives the thread is curved.

3. A suture package as in claim 1 wherein a portion of the needle-receiving means extends beyond at least one edge of the support element.

4. A suture package as in claim 1 wherein the needle-receiving means is a cylindrical body and the wrapping means is a cylindrical body of soft, nonsloughing foam material.

5. A suture package as in claim 1 comprising a plurality of needles received in the needle-receiving means and a length of surgical thread attached to each needle, each of the lengths of thread passing in the same direction about the wrapping means.

6. A suture package comprising:
   a relatively thin, stiff support element;
   a needle-receiving member mounted on the support element, the needle-receiving member comprising a body of a pierceable, nonsloughing material having a circular peripheral surface, the needle-receiving member being disposed on the support element with a portion thereof extending beyond an edge of the support element;
   a suture carried by the package, a portion of the suture needle being inserted into the peripheral surface of the needle-receiving member, the thickness dimension of the needle-receiving member being greater than the diameter of the needle;
   a wrapping member mounted on the support element, the wrapping member comprising a body having a circular peripheral surface; and
   a thread-retaining means on the support element, the surgical thread of the suture extending from the needle and passing about at least a portion of the peripheral surface of the wrapping member and thence to the thread-retaining means.

7. A package as in claim 6 wherein the suture is double-armed, the suture needles being oppositely disposed on the needle-receiving means and the surgical thread extending from each needle and wrapping about the wrapping member in the same direction and extending to the thread-retaining means.

8. A suture package comprising:
   a support element formed of a body of pierceable, nonsloughing foam material, the body having a cut-out portion extending along one edge thereof;
   thread-retaining means disposed along another edge of the body;
   a foldable sheet member having a portion to which the support element is secured and a portion foldable over the support element, the edge of the support element bearing the cut-out portion being disposed adjacent a fold between the respective portions of the sheet member;
   a suture associated with the package and including a needle retained at the cut-out portion of the support element, with a portion of the needle being received in a side edge of the body, the surgical thread of the suture extending from the needle, over a portion of the support means, and retained by the retaining means.

9. A suture package as in claim 8 wherein a plurality of needles are received in the recessed portion.